(12) United States Patent
Aksit et al.

(10) Patent No.: US 6,778,689 B1
(45) Date of Patent: Aug. 17, 2004

(54) SYSTEM AND METHOD OF REAL-TIME MULTIPLE FIELD-OF-VIEW IMAGING

(75) Inventors: Pelin Aksit, Baltimore, MD (US); J. Andrew Derbyshire, Columbia, MD (US); Ergin Atalar, Columbia, MD (US)

(73) Assignee: General Electric Company, Milwaukee, WI (US)

( * ) Notice: Subject to any disclaimer, the term of this patent is extended or adjusted under 35 U.S.C. 154(b) by 590 days.

(21) Appl. No.: 09/681,224

(22) Filed: Feb. 28, 2001

Related U.S. Application Data (60) Provisional application No. 60/193,401, filed on Mar. 29, 2000.

(51) Int. Cl.[7] .................................................. G06K 9/00
(52) U.S. Cl. ........................................ 382/128; 600/410
(58) Field of Search .............................. 382/128, 131, 382/154, 133; 600/407, 410; 378/4, 21; 128/922

(56) References Cited

U.S. PATENT DOCUMENTS

| | | | |
|---|---|---|---|
| 5,051,903 A | * 9/1991 | Pelc et al. | 324/309 |
| 5,697,370 A | 12/1997 | Pelc et al. | 128/653.2 |
| 5,907,593 A | 5/1999 | Hsieh et al. | 378/4 |
| 5,928,145 A | 7/1999 | Ocali et al. | 600/410 |
| 6,061,423 A | 5/2000 | Hsieh | 378/15 |
| 6,101,234 A | 8/2000 | Ali et al. | 378/4 |

OTHER PUBLICATIONS

Aksit et al., "Real Time Catheter Visualization Using Simultaneous Fluoroscopic MR Imaging on Multiple Channels at Multiple Fields of View", Proceedings of the World Congress on Medical Physics and Biomedical Engineering, 2000 (abstract) (1 page).*

Atalar et al., "Catheter–Tracking FOV MR Fluoroscopy", Magnetic Resonance in Medicine, 1998, vol. 40, pp. 865–872.*

* cited by examiner

*Primary Examiner*—Leo Boudreau
*Assistant Examiner*—Ryan J. Miller
(74) *Attorney, Agent, or Firm*—Ziolkowski Patent Solutions Group, LLC; Michael A. Della Penna; Carl B. Horton (57) ABSTRACT

A real-time imaging and visualization method and system that allows multiple field-of-view imaging on multiple receiver channels is disclosed. The method and system implement a semi-bit reversed modified phase-encoding scheme to acquire identical data over all receiver channels, and to reconstruct independently on each channel an image thereby providing multiple FOV images. The method and system provide for real-time catheter tracking where separate receiver channels collect anatomical roadmap data, guidewire data, and catheter data. The present invention uses a loopless antenna to acquire projection images thereby allowing the entire antenna and structures within its diameter of sensitivity to appear as a bright signal and a long narrow connected region. The present invention allows for very narrow FOV imaging for guidewire and catheter channels as well as full FOV imaging for roadmap image reconstruction. Thus, multiple FOV images are displayed together, improving visualization of the interventional device placement.

29 Claims, 9 Drawing Sheets

SYSTEM AND METHOD OF REAL-TIME MULTIPLE FIELD-OF-VIEW IMAGING

CROSS REFERENCE TO RELATED APPLICATION

This application claims the benefit of prior U.S. Provisional Application Serial No. 60/193,401, filed Mar. 29, 2000 and entitled MULTIPLE FOV MR FLUOROSCOPY.

STATEMENT REGARDING FEDERALLY SPONSORED RESEARCH OR DEVELOPMENT

The U.S. Government may have certain rights in this invention pursuant to NIH grants ROI HL61672 and HL57483.

BACKGROUND OF THE INVENTION

The present invention relates generally to a method and system of magnetic resonance (MR) imaging, and more particularly, to a method and system of multiple field-of-view (FOV) imaging.

Intravascular magnetic resonance (MR) methods for imaging arterial walls with ultra-high resolution for plaque characterization are widely known. It is also well known that intravascular MR has superior contrast and resolution of the vessels and the vessel wall compared to that provided by other known intravascular imaging methods, such as, intravascular ultrasound and angioscopy.

To be able to accurately and fully utilize these benefits, visualization of the interventional device placement and the surrounding anatomy, with frequent updates, is essential. Percutaneous placement of the interventional devices, currently, is performed under x-ray fluoroscopy. This requires the presence of an x-ray fluoroscopy and an MR scanner in the same room, with a compatible table. The disadvantages are numerous and include: alternating between two imaging modalities can alter the position of the catheter; it is quite costly; and both the patient and the physician are exposed to harmful ionizing radiation. An MR fluoroscopy technique to visualize interventional procedures with high spatial and temporal resolution is therefore desirable.

Many innovative techniques have been developed to make MR-guidance of interventional procedures possible. Known techniques focus on actively tracking the tip of the interventional device. Despite excellent temporal resolution, the drawback is that the number of device points that can simultaneously be tracked is limited by the number of receiver channels available on the scanner, which may not be sufficient for steering guidewires in the complex vasculature, or for selectively targeting small vessels. In many cases, visualization of the entire catheter is desirable to ensure there is no buckling or folding. Furthermore, these techniques rely on a previously acquired roadmap image to aid in localization, which does not necessarily represent the anatomy accurately because of motion, and additional roadmap images may be acquired throughout the procedure.

Known methods combine interventional device and anatomical roadmap images from multiple channels, during MR guided interventional procedures. The combined image feature dynamic roadmap images, as well as interventional device images. However, this implementation does not allow independent control over each channel's data, and signal from interventional devices may be obscured by the higher signal from the surface coil when roadmap images from surface coils are combined with interventional device images that have lower signal content.

It would therefore be desirable to design an intravascular magnetic resonance system and method that allows independent control over each of a number of data channels to provide interventional device as well as anatomical mapping at a clinically useful frame rate.

SUMMARY OF INVENTION

The present invention provides a system and method of multiple field-of-view magnetic resonance imaging that overcomes the aforementioned drawbacks.

In accordance with one aspect of the present invention a method of real-time multiple field-of-view imaging is disclosed. The method includes acquiring a number of imaging data sets each including a plurality of imaging space data lines organized in a semi-bit-reversed pattern. Next, at least one image frame factor having an imaginary part and a real part is determined from the plurality of reorganized imaging space data lines. An image is then constructed from at least one image frame factor.

In accordance with another aspect of the present invention, a computer program to generate real-time multiple field-of-view images causes a computer to acquire imaging data having a plurality of k-space lines. When instructed, the computer program reorders the plurality of k-space lines in a semi-bit-reversed order and determines a real part and an imaginary part of each of the plurality of reordered k-space lines. Using the real part and the imaginary part of each of the plurality of reordered k-space lines, the computer program determines at least one image factor frame and constructs an image therefrom.

In accordance with yet another aspect of the present invention, a multiple field-of-view imaging system is disclosed. The system includes a number of data acquisition devices and a data processing workstation having a computer readable storage medium having thereon at least one computer program. The system further includes a data transfer interface configured to transfer imaging data from the data acquisition devices to the data processing workstation. A data receiver having at least one device channel and at least one mapping channel is further provided.

The computer program provided with the multiple field-of-view image system instructs the data acquisition device to acquire imaging data having a plurality of imaging lines in a semi-bit-reversed phase-order and to transfer that data to the data processing workstation via the data transfer interface. The computer program then causes the data processing workstation to reorder the plurality of imaging lines according to the semi-bit-reversed order and to determine a real and imaginary part of each of the plurality of reordered imaging lines. At least one image factor frame is then determined and used to reconstruct a magnetic resonance image.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention. In the drawings.

DETAILED DESCRIPTION

Figure 1:
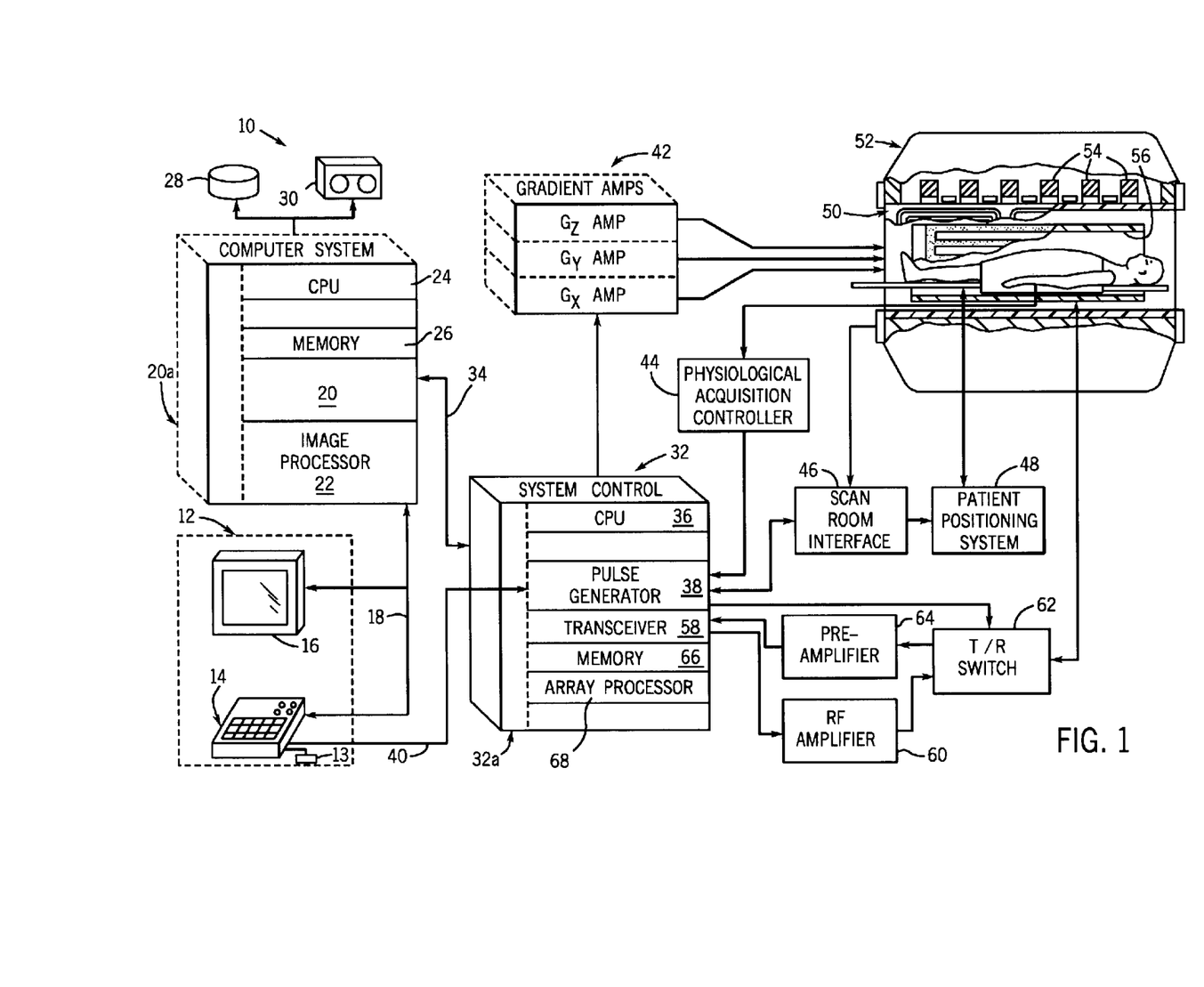
FIG. 1 is a schematic block diagram of an NMR imaging system for use with the present invention.

Referring to FIG. 1, the major components of a preferred MRI system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to a disk storage 28 and a tape drive 30 for storage of image data and programs, and it communicates with a separate system control 32 through a high speed serial link 34. The input device 13 can include a mouse, joystick, keyboard, track ball, touch screen, light wand, voice control, or similar device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator which indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 also receives patient data from a physiological acquisition controller 44 that receives signals from a number of different sensors connected to the patient, such as ECG signals from electrodes attached to the patient, or an interventional device, such as a catheter. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in an assembly generally designated 50 to produce the magnetic field gradients used for spatially encoding acquired signals. The gradient coil assembly 50 forms part of a magnet assembly 52 which includes a polarizing magnet 54 and a whole-body RF coil 56 or phased array coils. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 during the receive mode. The transmit/receive switch 62 also enables a separate RF coil (for example, a surface coil) to be used in either the transmit or receive mode.

The MR signals picked up by the RF coil 56 are digitized by the transceiver module 58 and transferred to a memory module 66 in the system control 32. When a scan is completed, an array of raw k-space data has been acquired in the memory module 66. As will be described in more detail below, this raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in the disk memory 28. In response to commands received from the operator console 12, this image data may be archived on the tape drive 30, or it may be further processed by the image processor 22 and conveyed to the operator console 12 and presented on the display 16.

Figure 2:
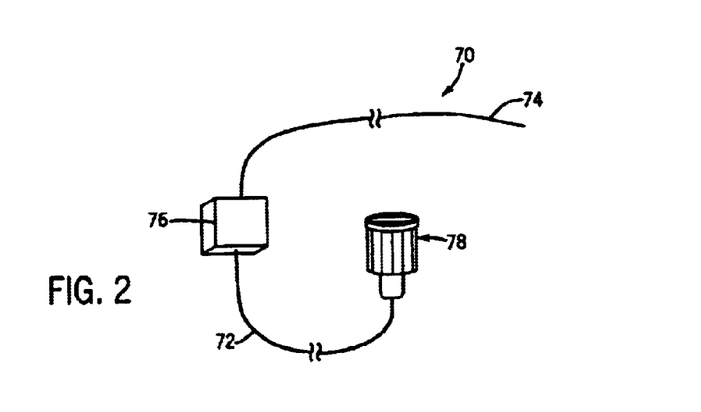
FIG. 2 is a perspective view of an interventional device for use with the present invention.

Referring to FIG. 2, and in a preferred embodiment, the present invention uses a loopless catheter antenna 70 to acquire projection images. The loopless antenna catheter 70 includes a coaxial cable 72 with an extended inner conductor 74, that acts essentially as a dipole antenna at the tip of the coaxial cable 72. The unbalanced currents on the coaxial cable 72 of the catheter 70 make visualization of the whole length of the catheter 70, as well as structures within its diameter of sensitivity possible. Its sensitivity decays approximately inversely with radial distance from the catheter center axis. Both the signal and the noise power detected by the antenna 70 are very high, which allows placing the tuning and matching circuitry 76 outside the body. Moreover, the electromagnetic properties of the antenna 70 are virtually independent of its size, unlike coils that incorporate a loop. The catheter antenna 70, which is essentially a wire, can be made very thin and flexible to allow insertion into very small tortuous vessels, while providing ultra-high resolution MR images with an extremely high sensitivity and SNR in its immediately vicinity. The catheter antenna 70 is connected to a data processing system (not shown) via connector 78. All of which is well known.

Alternatively, several other interventional device designs may provide catheter images that may be compatible with the present invention, such as a flexible catheter antenna or a gadolinium-coated catheter.

Figure 3:
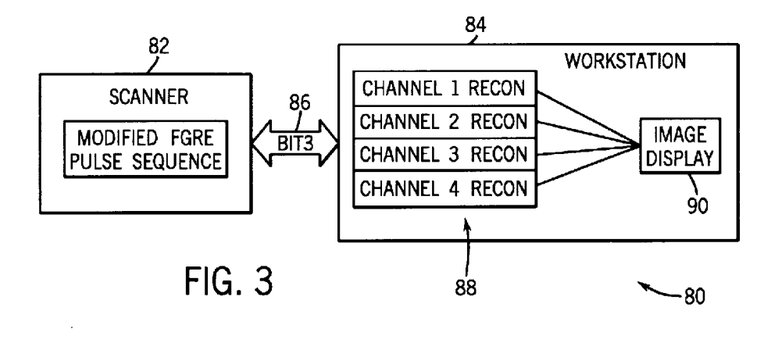
FIG. 3 is a schematic block diagram of a data processing system for use with the present invention.

Now referring to FIG. 3, a data processing system 80 implementing the present invention is shown. The data processing system 80 includes a scanner 82 and a workstation 84 having an image display 90 such as those disclosed with reference to FIG. 1. The workstation 84 is connected to the scanner 82 by a high bandwidth databus interface 86. Preferably, scanner 82 is a GE 1.5T CV/I MRI scanner, workstation 84 is a SUN ULTRA 2 Workstation, and high bandwidth databus 86 is a BIT3 interface. SUN ULTRA 2 is a registered trademark of Sun Microsystems of Mountain View, Calif. Scanner 82 continuously acquires imaging data, preferably with a fast gradient echo pulse sequence (FGRE), over any desired number of receiver channels. This raw data is transferred to the workstation over the BIT3 interface. The reconstruction of MR images and image manipulation and display are accomplished by the computer program running on the workstation 84.

Figure 4:
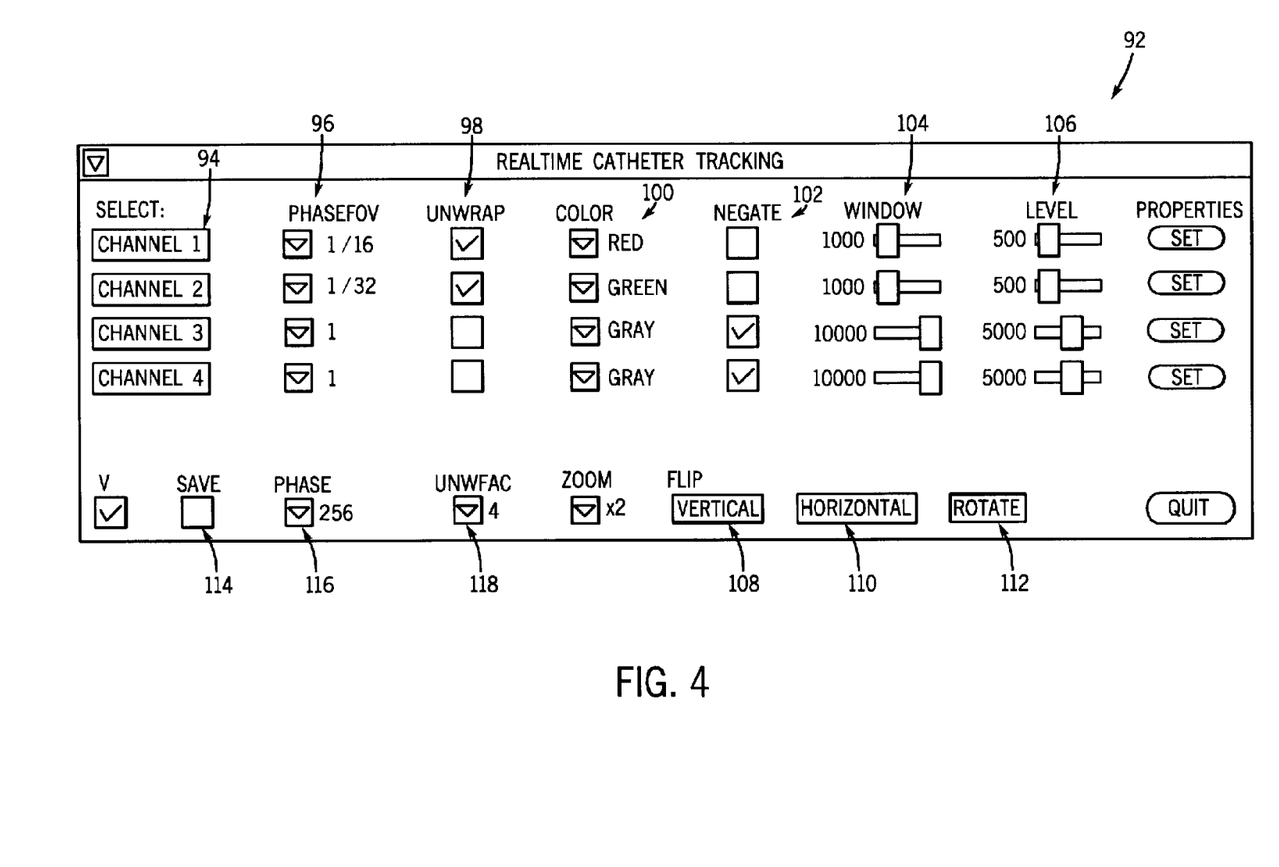
FIG. 4 is a representation of a graphical interface for use with the present invention.

A graphical user interface (GUI) 92, FIG. 4, allows a user to control the various preferences of the imaging system 80. The GUI 92 allows a user to change the operating parameters of each channel 88. In a four-channel embodiment, the GUI 92 includes a channel select 94 indicating the presence of four channels. The user can then change the phase field-of-view 96, indicate an unwrapping option 98, identify or assign a color 100, or negate a particular channel 102. Further, the user may set a window and level size 104, 106 as well as flip either vertically or horizontally as well as rotate the image 108, 110, and 112. The graphical interface 92 also provides a saving feature 114 that allows a user to save the selected operating parameters for each channel 98. GUI 92 further includes a phase number identification 16 as well as an unwrapping factor 118. The user may exit the operating parameter selection screen of the GUI 92 at 100. Additional features of the GUI 92 include indicators displaying the unwrapping rate for narrow field-of-view images and a threshold level and center offset for unwrapped catheter images.

The present invention maximizes the frame rate of interventional visualization in a new view-ordering technique that collects k-space data such that reconstruction of half, quarter, or $2^{-n}$ FOV images are possible during acquisition. This semi-bit-reversed view-ordering method allows for multiple-FOV imaging on multiple receiver channels, as well as multiple-FOV imaging within each channel. In a preferred embodiment, two of the four available MR receiver channels collect anatomical roadmap data while the other two are used to visualize a guidewire, and a catheter. Phase ordering is such that high frame rate images of the guidewire and catheter are reconstructed at $2^{-n}$ FOV, while roadmap data fills the k-space for appropriate full FOV images. As data is acquired, each channel is reconstructed independently with the flexibility of choosing a different field-of-view according to what is being imaged on a certain channel, narrow-FOV for catheter/guidewire channels, and large-FOV for roadmap channels. Very narrow FOV images are used to provide real-time catheter tracking with a high temporal resolution, and large FOV images will provide a dynamic roadmap image with a lower temporal resolution. Small subsets of the k-space are acquired to provide fast updates of the catheter with the accumulation of such subsets filling the k-space with appropriate data to reconstruct a full FOV roadmap image. A semi-bit-reversed phase order is disclosed to accomplish the reconstruction of half, quarter, or $2^{-n}$ FOV images during acquisition.

Small sets of equally spaced k-space lines are acquired linearly. Each such set comprises sufficient data to reconstruct a narrow FOV image. A data set can also be interleaved with subsequent sets such that after acquisition of any power of 2 small sets, all k-space lines will be equally spaced with uniform sampling. The n number of k-space lines in each small set depends on the minimum FOV required for successful unwrapping of a catheter image. The size m of each small set should be a divisor of the total number of phase-encode lines, such that the result is a power of 2, to allow multiple FOV imaging in accordance with:

$$Npe/m = 2^n, n = 0, 1 \ldots, \log^2 (Npe/m) - 1, \quad \text{(Eqn. 1)}$$

Where Npe is the total number of phase-encode lines, and m is the number of phase-encode lines in each set. After the acquisition of $2^n$ (n=0, 1 ... $\log^2$ (Npe/m)) small sets, all k-space lines will be equally spaced, and the combination can be used to form an image with $2^{-n}$ the full FOV and $2^n$ higher frame rate. For instance, for a 256-line k-space acquisition, eight lines is the smallest number of k-space lines necessary for successful unwrapping of a catheter image. This results in a 32-fold reduction in FOV, and 32-fold increase in the frame set of the catheter movie. Each such set of eight lines is sufficient to produce one frame of a very narrow FOV catheter movie. Consecutive sets can also be joined to increase the FOV of the entire movie, or a section of the movie.

Figure 5:
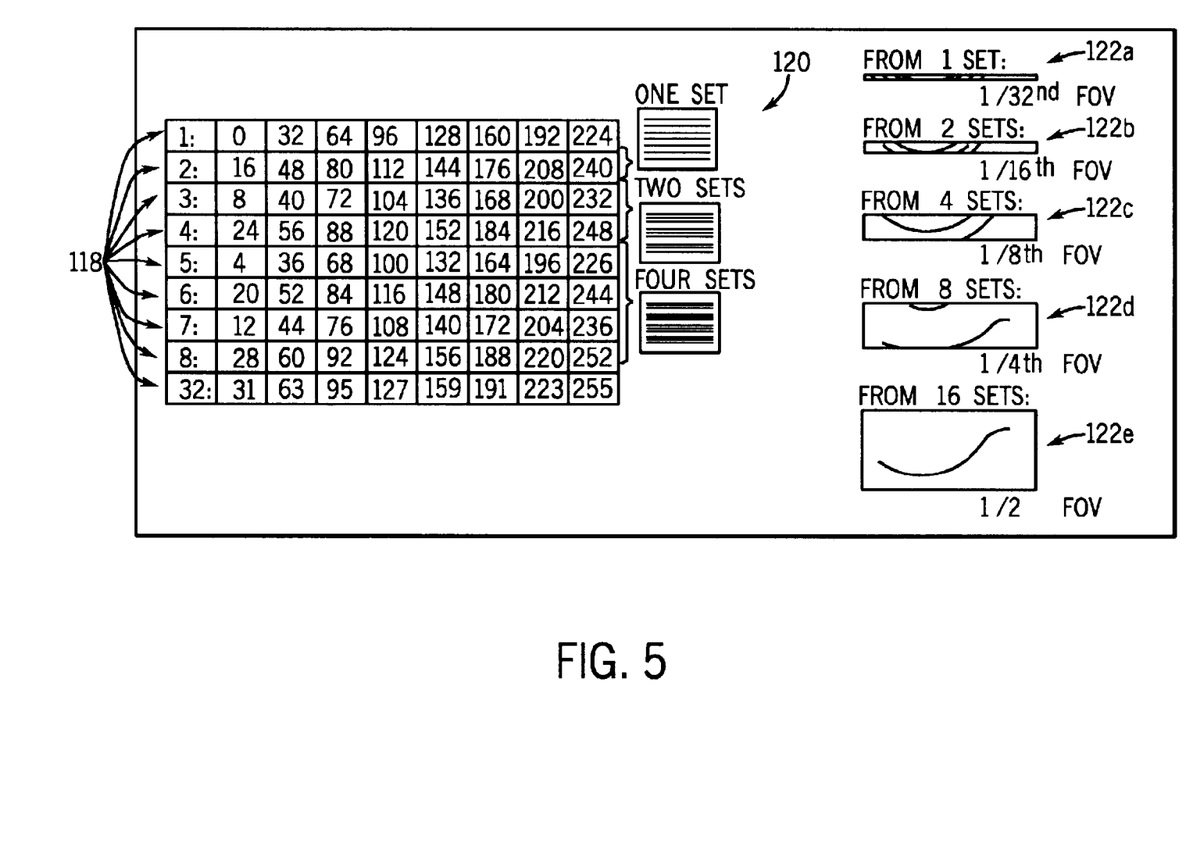
FIG. 5 is a representation of a multi-dimensional data array in accordance with the present invention.

Now referring to FIG. 5, each small set of k-space lines 118 is acquired linearly to minimize ghosting of the linearly moving catheter image. Consecutive sets are then interleaved to provide maximum equal spacing among the collected data over time. This leads to a semi-bit reversed phase-order, which will be explained with the example of 256 k-space lines 18 acquired in small sets of eight (the first eight sets, and the last set are shown). On the right side of the FIG. 120, k-space lines representing the acquired data, and possible larger groupings are shown. Images reconstructed with different size groupings 122a–122e of this data are also shown in FIG. 5. Each set is reconstructed and displayed individually, to produce one frame of catheter or guidewire images with $\frac{1}{32}$ of the full FOV. In this case, the temporal resolution is 8*TR. Two consecutive sets are combined to create an image with $\frac{1}{16}$ the FOV, if eight k-space lines are insufficient for successful unwrapping. Temporal resolution in this case is 16*TR. Similarly, larger groupings can be used to create images with a larger FOV at the expense of reduced temporal resolution. To reconstruct the full FOV image without sacrificing spatial resolution, all of the k-space must be sampled. This means acquisition of all 32 sets of eight k-space lines, resulting in a temporal resolution of 256*TR between frames. Although the temporal resolution of this large image is 256*TR, large FOV images can be updated as each new set is acquired at intervals of 8*TR, providing a smoother transition over time.

Figure 6:
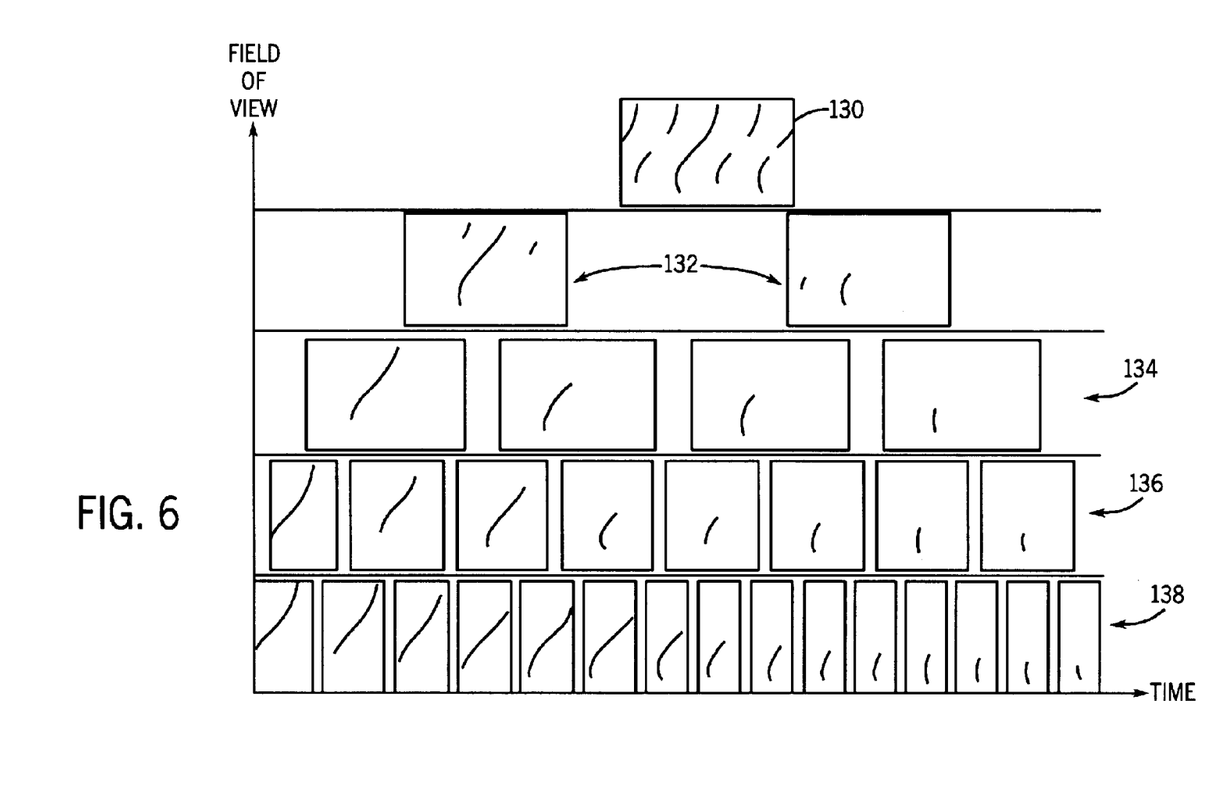
FIG. 6 is a representation of various field-of-view images in accordance with the present invention.

FIG. 6 shown in color inversion for the purpose of illustration provides a representation of the increase in temporal resolution of an image by narrowing its FOV. The catheter appears as a dark line, while the surrounding saline solution appears as a white background. The phantom includes an S-shaped tube that was immersed and fixed in a bath of saline solution. The catheter was retracted while data was being acquired with the semi-bit-reversed phase order. The tip of the catheter is at the top of the images, and it exits from view at the bottom. A modified fast gradient echo pulse sequence was used for the acquisition of 256 lines of k-space data (TR/TE 5/1.6 ms, FOV: 24 cm, 256×256 partial NEX). The images were reconstructed from different groupings of the same data. The full FOV image was reconstructed by combining all 32 sets of 8 k-space lines. Image 130, 131 of FIG. 6 shows ghosting due to the motion of the catheter during the data acquisition time of 1.28 seconds, which corresponds to a frame rate of 0.78 frames/second 130. When the same data is split into even and odd lines of the k-space, two ½-FOV images are obtained 132. The temporal resolution doubles, and the large jump of the catheter is visible in the unwrapped frames. The frame rate of these two frames 132 is 1.56 frames/second (temporal resolution=640 ms). When every $4^{th}$ line of k-space is used for reconstruction, four distinct frames 134 with ¼ the FOV from the same amount of data are obtained to form full FOV images. The temporal resolution quadruples, and more details of the catheter motion are visible on the unwrapped frames (temporal resolution 320 ms, frame rate=3.12 frames/second). The same trend continues with ⅛ and ⅟₁₆ the FOV frames 136, 138. The very narrow non-rectangular FOV, follows the catheter as it moves out of view at 6.14 frames/second (temporal resolution=160 ms, and 12.5 frames/second (temporal resolution=80 ms), respectively.

The effective FOV required for successful unwrapping of the catheter or guidewire image depends on the diameter of the interventional device, its alignment, and overall image quality. If the catheter aligns primarily in the phase-encoding direction, the catheter image wraps onto itself, and the FOV must be increased until the ambiguity is resolved. However, if a part of the catheter forms a loop, such as a pigtail shape, the frame rate of the entire movie does not need to be decreased to eliminate ambiguity in that part of the image. The phase-encoding algorithm described allows imaging with different frame rates for different parts of the object.

A 2-D Fourier transform of the k-space data is used to reconstruct the image. This is equivalent to applying a 1-D Fourier transform in the readout direction, followed by another 1-D Fourier transform in the phase-encoding direction. The first Fourier transform rearranges k-space data along the readout direction such that data becomes spatially resolved in that direction, and there is a one-to-one correspondence between distinct portions of the catheter image and the 1-D Fourier transformed data. At this point, constant FOV catheter images are produced with the data that is available or variable FOV catheter image is constructed by regionally increasing the FOV of certain catheter sections. With a variable FOV image, the FOV in the phase-encoding direction varies as a function of position in the frequency encoding direction.

In another preferred embodiment multiple field-of-view imaging is allowed on multiple receiver channels. In this embodiment a dynamic anatomical roadmap image is also provided for guidance of interventional devices. Using the method to be described, this can be accomplished without compromising the spatial resolution of anatomical images, or the temporal resolution of interventional device images, Most commercially available MR scanners are equipped with at least four receiver channels that can simultaneously acquire image data from separate receiver coils according to a prescribed pulse sequence. In addition to viewing the catheter or guidewire at very high frame rates, the present invention can provide a dynamic roadmap image using these available scanner resources. Accordingly, excitation of the MR pulse results in identical data acquisition over all channels. Two or three channels collect data through phased array surface coils for a roadmap image, while the other channels are connected to an active guidewire and an active catheter.

In this embodiment, raw data is acquired with the semi-bit-reversed phase order and automatically transferred to the workstation directly connected to the MR scanner after acquisition of each small set of k-space lines. Each channel is then reconstructed independently at different FOVs, and later combined for display on the workstation.

On the guidewire and catheter channels, data is reconstructed as soon as a set of imaging lines is acquired (up to 25 frames/second). For the roadmap channels, it is necessary to wait for sufficient data to form a large FOV image to avoid aliasing of the complex structures of the surrounding anatomy (1.56 frames/second).

A fast gradient echo pulse sequence (FGRE) is modified as previously described such that the view-ordering table is recalculated to acquire phase-encoded data in a semi bit-reversed fashion. Small sets of equally spaced k-space lines are acquired linearly, followed by another small set, interleaved with the previous set. In addition to changing the phase-ordering table on the pulse sequence, a Real-Time Process (RTP) is programmed within the FGRE, to make this data available on a workstation 84, FIG. 3. This option of making data available to the workstation is activated by a control variable on the scanner console. The steps of the method and the acts of the one or more computer programs provide that acquisition, data transfer, reconstruction, and display are to be interrupt-driven to avoid any delays or inconsistencies in timing associated with polling.

Figure 11:
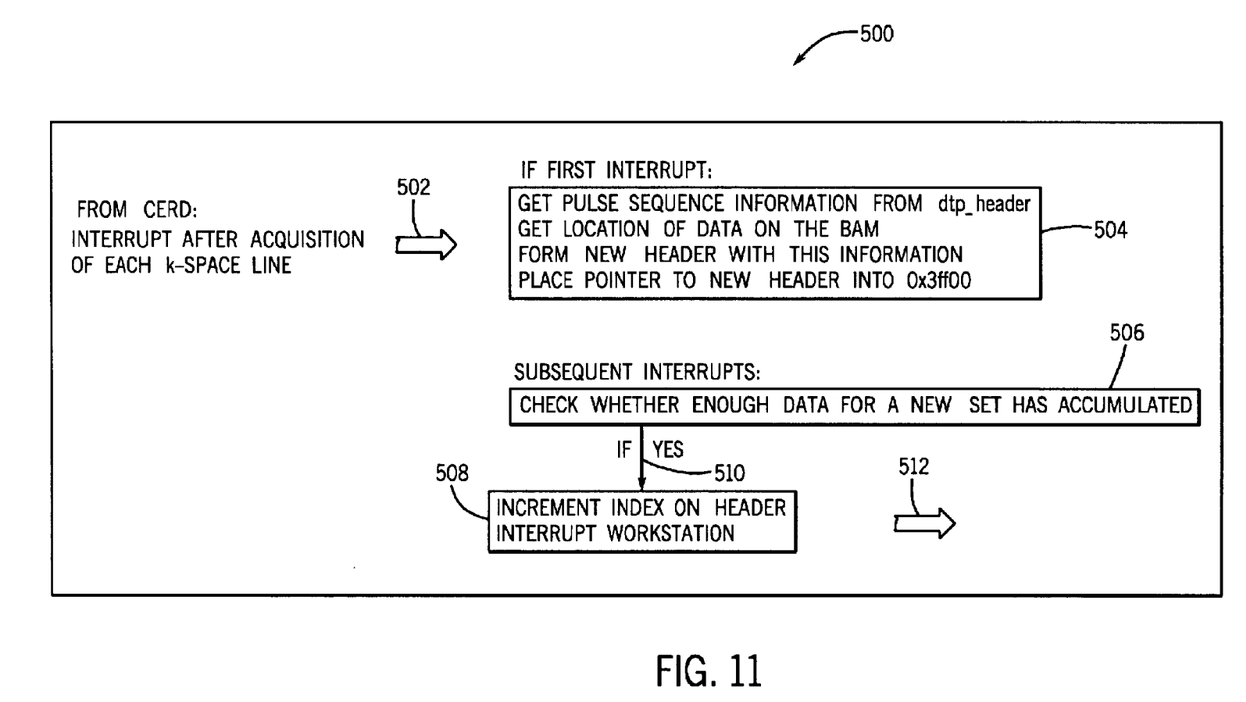
FIG. 11 is another flow chart in accordance with the present invention.

The Integrated Pulse Generator (IPG) provides appropriate excitation and gradients, and a Combined Exciter Receiver Data Acquisition Board (CERD) receives a corresponding MR signal. Once this data is saved on Bulk Access Memory (BAM), rather than signaling a Transceiver Processor and Storage (TPS) process for standard reconstruction, the RTP signals the TPS to execute a TPS program. This TPS program is illustrated by the flow chart of FIG. 11. The TPS program 500 receives an interrupt from the CERD after acquisition of each k-space line 502. The TPS program also accesses information regarding where in BAM the data is located, as well as pulse sequence specific information. A header is formed within the FGRE, and contains information about the acquisition, such as the x, y, z, resolution, data size, size of the linear sets of data, number of such sets to be acquired, and the number of receivers collecting data. When the first RTP interrupt is received by the TPS program, another header is created 504 with this information and the location of the data and an index indicating how many sets of data have been acquired. A pointer is placed to this new header in memory of the TPS. In a preferred embodiment, 256 bytes of TPS memory located in a memory registry are used. On subsequent interrupts, the TPS program counts the number of interrupts received 506, and increments the corresponding index of the header 508. When a desired number of k-space lines have accumulated 510, 8 in a preferred embodiment, an interrupt 512 is generated over a BIT3 interface to alert the workstation of the availability of a new set of data. However, one skilled in the art will appreciate that other numbers of k-space lines for increased flexibility of implementation may be used as a minimum in accordance with Equation 1.

Data is transferred from scanner BAM to a raw data memory location or buffer on the workstation. The RawdataBuffer consists of a header having information about the most recently acquired set of imaging data, identification pointers to other steps in the reconstruction process for each channel, and a circular data buffer with sufficient available memory to hold a full FOV image from each active receiver channel. Raw data is accessed from the RawdataBuffer, and reconstructed images are placed in a RealtimeBuffer. The RealtimeBuffer consists of a header for each channel with reconstruction and display preferences from the user selected via the graphical user interface, and a circular buffer with sufficient memory to store 20 images for each channel. A display program is also provided and responsible for combining and manipulating images for each receiver channel.

Figure 7:
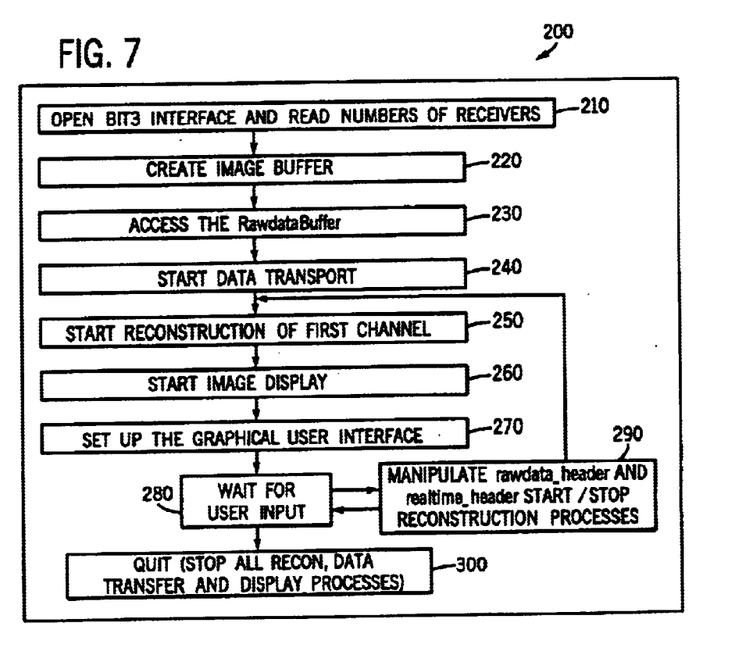
FIG. 7 is a flow chart for use with the present invention.

Now referring to FIG. 7, a flow chart summarizing the steps of a method as well as the acts of one or more computer programs to facilitate image reconstruction is shown. Image reconstruction begins at 210 by determining a number of active receiver channels of a scanning device from a data header in TPS memory and the opening of a BIT3 interface device. An image buffer is created at 220 and a data buffer is accessed at 230. A data transport algorithm is activated for the first channel at 240. In a preferred embodiment, eight lines of k-space data are transferred by the data transport algorithm to the raw data buffer accessed at 230 immediately upon data acquisition. A corresponding index indicating the transference of the data is incremented on a raw data header in memory. When sufficient data for a desired field of view image has accumulated and been received, an interrupt is sent at 240. Data is obtained from the raw data buffer at 250 and image reconstruction begins according to user-defined preferences. Image reconstruction continues at 250 until a final image is placed into the real-time buffer created at 220 with an image display algorithm beginning at 260. Reconstruction and display steps 250, 260 communicate via a first-in, first-out pipe (not shown). Once reconstruction 250 is complete, a channel number corresponding to the data being reconstructed is written into the first-in, first-out pipe. When a new image is available, the image is displayed according to the user specifications on that channel as established with the graphical user interface 270. User input is received at 280 and the data is manipulated accordingly at 290. Start and stop reconstruction commands are also processed at 290. Each receiver channel has a header designation, which contains reconstruction instructions, as well as display instructions. The reconstruction instructions include whether the channel is ON/OFF, spatial resolution of the incoming data, desired field-of-view of the channel, whether unwrapping is necessary, the threshold level, and center-offset for unwrapped catheter images. By default all receiver channels are reconstructed at a full field-of-view since initially channels corresponding to the guidewire and the catheter are unknown. Once found, however, catheter and guidewire data are reconstructed upon data acquisition wherein the reconstruction completes at 300.

Now referring to FIG. 8, the steps and acts comprising step 240 of FIG. 7 will be discussed in greater detail. At 241, the BIT3 interface is enabled to allow the transfer of imaging data. At 242, a data header is read indicating the presence of imaging data. If a raw data buffer does not exist, one is created at 243 as a storage location in memory for storing the transferred imaging data. A raw data header is written into the raw data buffer at 244 to properly identify the raw data buffer for subsequent processing. At 245, the most recent data set received through the BIT3 interface is copied into the raw data buffer. Next, the method determines how many small sets of data have been received 246 and generates an appropriate signal for each active channel if enough data for that channel is available for image reconstruction. If sufficient sets of data are present, an interrupt is generated at 248 signaling the active channel that enough data is present for image reconstruction. If sufficient data for image reconstruction is not available then the method pauses at 246 until sufficient data has arrived. Once sufficient data has been accumulated the interrupt is generated at 248.

Figure 8:
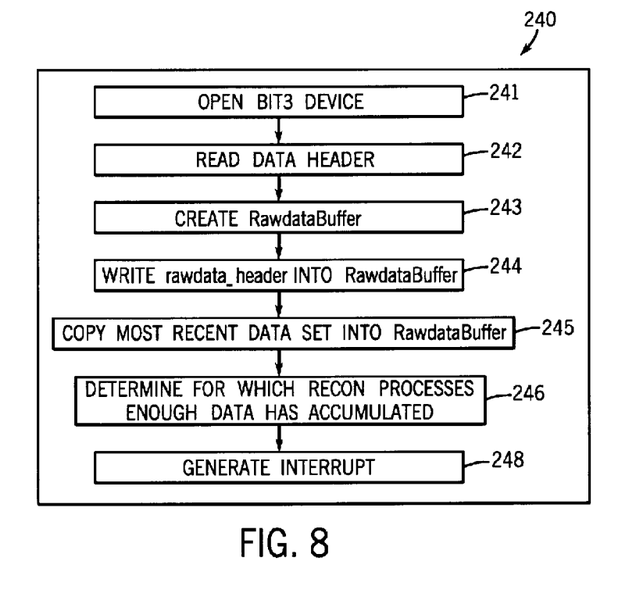
FIG. 8 is another flow chart for use with the present invention.
Figure 9:
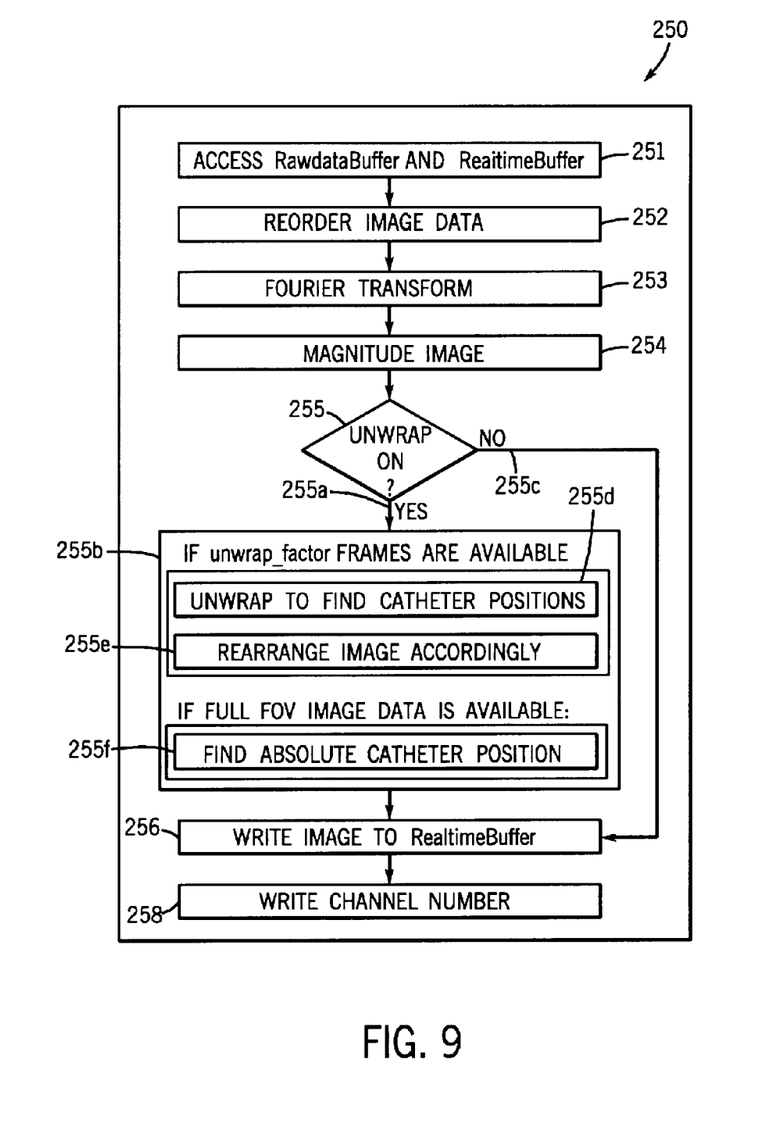
FIG. 9 is another flow chart in accordance with the present invention.

Once an interrupt signal is generated at 248, FIG. 8, image reconstruction begins at 250, FIG. 7. The steps associated with image reconstruction step 250 will now be discussed in greater detail with reference to FIG. 9. Reconstruction of a first channel 250 begins with the accessing of the raw data and real-time buffers at 251. At 252, the image data is reordered according to a semi-bit reversed pattern. A two-dimensional Fourier transform is applied at 253 to facilitate image reconstruction. At 254, a magnitude-squared image is calculated from the real and imaginary images obtained from the Fourier transform 253. Next, the method determines if an unwrapping feature is ON at 255. If the unwrapping feature is activated at 255 then the method proceeds at 255a and determines at 255b if unwrapping factor frames or a full field-of-view image data set are available. If the unwrapping option is not activated at 255 then the method proceeds at 255c to writing the determined magnitude image at 254 to a real-time buffer 256. Unwrapping of a narrow FOV image may be done on an image by image basis, or by using information from previous image frames as well as the current image. The number of previous image frames that are included in the unwrapping algorithm is named the "unwrapping factor". Referring to 255b, if "unwrapping factor" frames are available then these frames are unwrapped at 255d to determine catheter positions and the image is rearranged accordingly at 255e. If a full field-of-view image data set is available the absolute catheter position is determined at 255f. The resulting image at 255e and 255f are written to the real-time buffer at 256 whereupon the channel number is written 258 to the image display at 260, FIG. 7.

Figure 10:
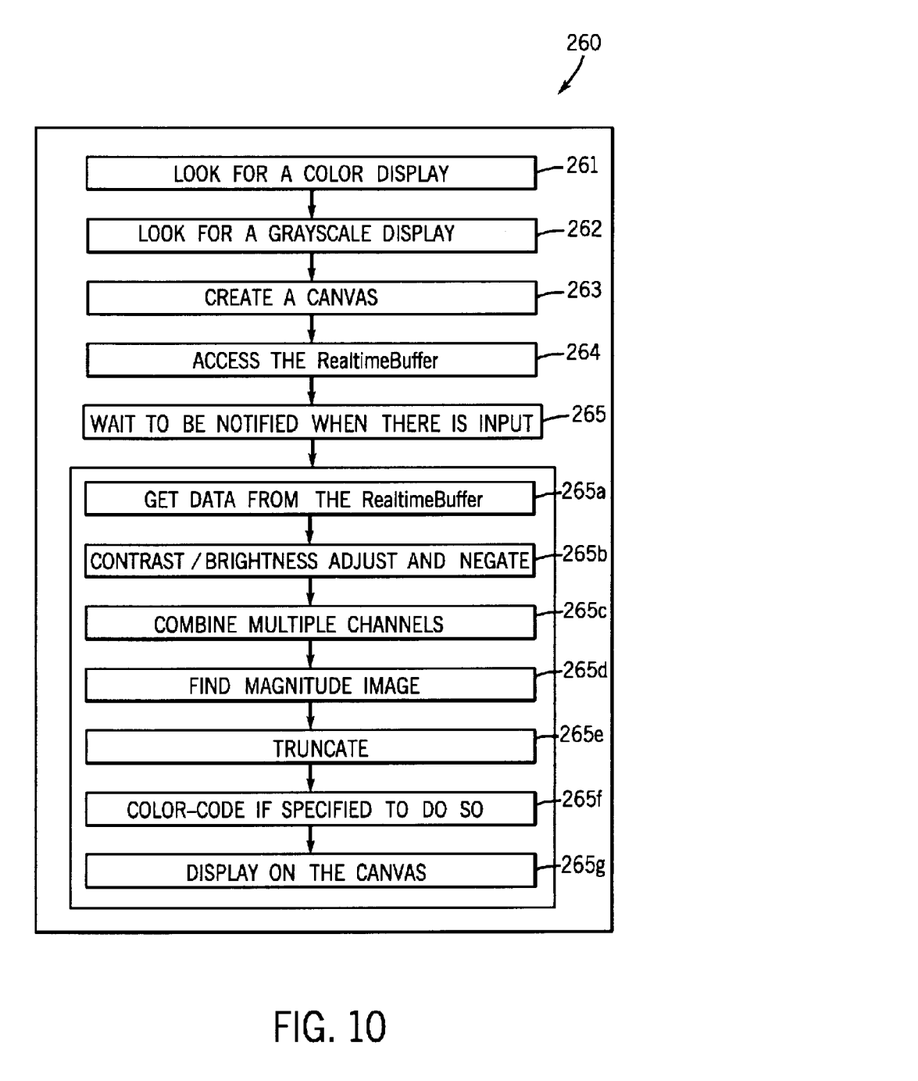
FIG. 10 is yet another flow chart in accordance with the present invention.

The image display step 260, FIG. 7, will now be discussed in greater detail with particular reference to FIG. 10. The image display control 260 begins at 261 with a determination of whether a color display is available. If not, a gray-scale display is implemented at 262. A canvas is created at 263 and the real-time buffer is accessed at 264. At 265, the method determines if there is input in the real-time buffer. Once notified at 265, data is accessed from the real-time buffer at 265a and the contrast/brightness are adjusted and/or negated at 265b. At 265c, multiple channels of the workstation are combined and the square root of the combined sum is determined at 265d. At 265e, the data accessed from the real-time buffer at 265 is truncated so that in a preferred embodiment, only 256 bits are used. If instructed to do so, the combined image is color-coded at 265f and magnified if further instructed. At 265g the image is displayed on the canvas created at 263. After the image is displayed on the canvas at 265g the method proceeds to setting up the graphical user interface at 270, FIG. 7.

For catheter and guidewire images, the degree of image overlap depends on the apparent width of the interventional device, and its orientation with respect to the phase-encoding direction. The unwrapping algorithm is typically turned on for images with a $\frac{1}{4}^{th}$ FOV. When aliasing in the phase-encoding direction is allowed, there is an ambiguity in the absolute position of the catheter. The resulting images may be shifted by exactly n*Ny, any multiple (n) of the number of phase encode steps (Ny). As soon as enough data to form a full FOV image arrives, this ambiguity is resolved by calculating the correct catheter position, and automatically determining n. All other images are registered using the information from previous frames and ambiguity is eliminated. Once unwrapping is complete, the narrow FOV image is rearranged to place the catheter on the center of the displayed image. The reconstructed (and unwrapped) image is then placed into an image buffer, and the display step is signaled to refresh the image.

The present invention discloses a multiple field-of-view imaging system including a number of data acquisition devices and a data processing workstation having a computer readable storage medium having thereon at least one computer program to facilitate image reconstruction. The system further includes a data transfer interface configured to transfer imaging data from the data acquisition devices to the data processing workstation. A data receiver having at least one device channel and at least one mapping channel is also provided. The at least one computer program stored within the data processing workstation causes the workstation to acquire imaging data from the data acquisition device through the data transfer interface. The imaging data has a plurality of imaging lines which are reordered in a semi-bit-reversed fashion by the computer program. A Fourier transform is implemented to determine a real and an imaginary part of each of the plurality of reordered imaging lines so that at least one image factor frame may be determined. The at least one image factor frame is then used by the data processing workstation to construct an MR image. The system further includes a graphical user interface having a number of reconstruction controls such as an ON/OFF control, a field-of-view selector, a threshold level control, an unwrapping selector, a spatial control, and a center offset control.

The implementation of the present invention further contemplates the use of more than one interventional device at a time. Essentially, the present invention is only limited by the number of channels of the scanning device. Regardless of the multitude of channels, channels may be combined or turned off in accordance with the present invention depending on the visualization a user requires for a particular channel.

The present invention has been described in terms of the preferred embodiment, and it is recognized that equivalents, alternatives, and modifications, aside from those expressly stated, are possible and within the scope of the appending claims.

What is claimed is:

1. A method of real-time multiple field-of-view (FOV) imaging comprising the steps of:
    acquiring a number of imaging data sets, each including a plurality of imaging space data lines;
    organizing the plurality of imaging space data lines of the number of imaging data sets in a semi-bit reversed pattern;
    determining at least one image frame factor having an imaginary part and a real part; and
    reconstructing an image from the at least one image frame factor.

2. The method of claim 1 wherein the data sets are MR data sets and further comprising the step of displaying the reconstructed image.

3. The method of claim 1 further comprising the step of determining an interventional device position with the reconstructed image.

4. The method of claim 3 further comprising the step of unwrapping the at least one image frame factor to determine the interventional device position.

5. The method of claim 1 further comprising the step of selecting a field-of-view before acquiring a number of imaging data sets.

6. The method of claim 5 further comprising the step of determining a number of the plurality of imaging space data lines necessary for the selected field-of-view.

7. The method of claim 1 further comprising the step of applying a Fourier transform to the plurality of imaging space data lines in a phase encoding direction and mapping between the plurality of imaging space data lines and the reconstructed image.

8. The method of claim 1 further comprising the step of combining a number of the plurality of imaging space data lines with a multi-channel receiver to enlarge a selected field-of-view.

9. A computer readable medium storing a computer program to generate real-time multiple FOV images that when executed by a processor causes a computer to:
    acquire image data having a plurality of k-space lines;
    reorder the plurality of k-space lines in a semi-bit reversed order;,
    determine a real part and an imaginary part of each of the plurality of reordered k-space lines;
    determine at least one image factor one; and
    construct an image from the at least one image factor frame.

10. The computer readable medium storing a computer program of claim 9 that when executed further causes the computer to display the reconstructed image.

11. The computer readable medium storing a computer program of claim 9 that when executed further causes the computer to determine if a full field-of-view image data set is available.

12. The computer readable medium storing a computer program of claim 11 that when executed further causes the computer to determine an absolute device position.

13. The computer readable medium storing a computer program of claim 9 that when executed further causes the computer to unwrap the at least one image factor frame.

14. The computer readable medium storing a computer program of claim 9 that when executed further causes the computer to select a field-of-view and further determine a minimum number of the plurality of k-space lines needed for the selected field-of-view.

15. The computer readable medium storing a computer program of claim 14 that when executed further causes the computer to combine a number of the plurality of k-space lines to enlarge the field-of-view.

16. The computer program of claim 9 that when executed further causes the computer to generate a signal indicating that the imaging data has been acquired.

17. A multiple field-of-view (FOV) imaging system comprising:
    a number of data acquisition devices;
    a data processing workstation having a computer readable storage medium having thereon at least one computer program;
    a data transfer interface configured to transfer imaging data from the number of data acquisition devices to the data processing workstation;
    a data receiver having at least two receiver channels including at least one device channel and at least one mapping channel;
    wherein the at least one computer program when executed causes the data processing workstation to:
        acquire imaging data having a plurality of imaging lines from the data acquisition device through the data transfer interface;
        reorder the plurality of imaging lines in a semi-bit reversed order;
        determine a real part and an imaginary part of each of the plurality of reordered imaging lines;
        determine at least one image factor frame; and
        reconstruct an image from the at least one image factor frame.

18. The system of claim 17 further comprising a graphical user interface (GUI) having a number of reconstruction controls including a channel ON/OFF control, a field-of-view selector, a threshold level control, an unwrapping selector, a spatial control, and a center offset control.

19. The system of claim 17 wherein the number of data acquisition devices includes a loopless antenna interventional device and a guidewire.

20. The systems of claim 17 wherein the data processing workstation linearly generates a phase ordering table.

21. The system of claim 17 wherein the data processing workstation displays an MR image from the at least two receiver channels.

22. The system of claim 17 wherein the computer program when executed further causes the data processing workstation to determine if a full field-of-view image data set is available.

23. The system of claim 17 wherein the computer program when executed further causes the data processing workstation to determine an absolute device position with improved visualization.

24. The system of claim 17 wherein the computer program when executed further causes the data processing workstation to unwrap the at least one image factor frame.

25. The system of claim 17 wherein the computer program when executed further causes the data processing workstation to select a field-of-view and further determine a minimum number of a plurality of k-space lines needed for the selected field-of-view.

26. The system of claim 17 wherein the computer program when executed further causes the data processing workstation to combine a number of a plurality of k-space lines to enlarge a field-of-view.

27. The system of claim 17 wherein the computer program when executed further causes the data processing workstation to generate a signal indicating that the imaging data has been acquired.

28. The system of claim 17 wherein the computer program when executed causes the data processing workstation to display an image of a catheter with a reduced field-of-view having a high frame rate and a high temporal resolution on the at least one device channel.

29. The system of claim 28 wherein the computer program when executed causes the data processing workstation to display an anatomical mapping image with a full field-of-view having a lower frame rate on the at least one mapping channel.

* * * * *

UNITED STATES PATENT AND TRADEMARK OFFICE
CERTIFICATE OF CORRECTION

PATENT NO. : 6,778,689 B1
DATED : August 17, 2004
INVENTOR(S) : Aksit et al.

It is certified that error appears in the above-identified patent and that said Letters Patent is hereby corrected as shown below:

Column 12,
Line 9, delete "one" and substitute therefor -- frame --.

Signed and Sealed this

Twelfth Day of October, 2004

JON W. DUDAS
*Director of the United States Patent and Trademark Office*